United States Patent [19]
Fischell et al.

[11] Patent Number: 5,730,698
[45] Date of Patent: Mar. 24, 1998

[54] BALLOON EXPANDABLE TEMPORARY RADIOISOTOPE STENT SYSTEM

[76] Inventors: Robert E. Fischell, 14600 Viburnum Dr., Dayton, Md. 21036; David R. Fischell, 71 Riverlawn Dr., Fair Haven, N.J. 07704; Tim A. Fischell, 1018 Chancery Dr., Nashville, Tenn. 37215

[21] Appl. No.: 437,400

[22] Filed: May 9, 1995

[51] Int. Cl.[6] .............................. A61M 25/10; A61N 5/00
[52] U.S. Cl. .............. 600/3; 608/108; 608/198; 608/194; 608/104
[58] Field of Search .................... 600/1–7; 604/102, 604/108, 95–97, 160, 194, 198, 22, 28; 606/8, 159, 191, 194–198, 200

[56] References Cited

U.S. PATENT DOCUMENTS

| | | | |
|---|---|---|---|
| 4,921,484 | 5/1990 | Hillstead | 606/194 X |
| 4,929,602 | 5/1990 | Harker et al. | 514/18 |
| 5,002,560 | 3/1991 | Machold et al. | 606/198 |
| 5,034,001 | 7/1991 | Garrison et al. | 604/53 |
| 5,059,166 | 10/1991 | Fischell et al. | 600/3 |
| 5,109,859 | 5/1992 | Jenkins | 128/662.03 |
| 5,217,474 | 6/1993 | Zacca et al. | 606/159 |
| 5,302,168 | 4/1994 | Hess | 600/3 |
| 5,338,296 | 8/1994 | Dalessandro et al. | 604/96 |
| 5,342,348 | 8/1994 | Kaplan | 606/198 X |
| 5,441,516 | 8/1995 | Wang et al. | 606/198 |
| 5,484,384 | 1/1996 | Fearnot | 600/3 |
| 5,484,449 | 1/1996 | Amundson et al. | 606/194 X |

FOREIGN PATENT DOCUMENTS

0533511A1  3/1993  European Pat. Off.

*Primary Examiner*—John P. Lacyk
*Assistant Examiner*—Stephen Huang
*Attorney, Agent, or Firm*—Morton J. Rosenberg; David I. Klein; Jun Y. Lee

[57] ABSTRACT

An expandable temporary stent system (10) is provided for creating a temporary stent within a vessel of a human body and includes an over-the-wire balloon angioplasty catheter (20) having a central lumen (26) and a distal section having an inflatable balloon (23). The balloon angioplasty catheter (20) has a proximal section that remains outside the body. A stent assembly (30) is slidably mounted on the balloon angioplasty catheter (20) in a coaxial manner and has a proximal section as well as a distal section where a temporary stent (31) is located at the distal section. The distal end of the stent assembly (30) is fixed to the distal section of the balloon angioplasty catheter (20). The proximal end of the temporary stent (31) is fixed to a distal end of a pusher tube (32). The pusher tube (32) cooperates with the proximal section of the balloon angioplasty catheter (20) and allows the temporary stent (31) to be reversibly deployed in a radial outward manner responsive to inflation of the balloon and, retracted so that the temporary stent (31) reforms around the balloon (23) of the balloon angioplasty catheter (20) for providing blood flow through the vessel and removal of the system from the vessel of the human body.

20 Claims, 12 Drawing Sheets

BALLOON EXPANDABLE TEMPORARY RADIOISOTOPE STENT SYSTEM

FIELD OF USE

This invention is in the field of radioisotope stents that are inserted into a vessel of a human body to help create and maintain the patency of that vessel.

BACKGROUND OF THE INVENTION

Intravascular stents are regularly inserted into human arteries and other vessels to create and maintain the patency of that vessel. Furthermore, as taught in U.S. Pat. Nos. 5,059,166 and 5,176,617 by R. E. and T. A. Fischell, a stent that is radioactive can reduce intimal proliferation from a balloon dilated arterial stenosis and therefore can reduce restenosis. However, the stents taught by the Fischells are permanent implants which may not be a good long term treatment particularly for arteries whose normal diameter is less than 3.0 mm. Furthermore, stents are not able to be placed at each and every dilated stenosis. Specifically, permanent stents are not suitable at some bifurcation stenoses nor are they suitable when a side branch of the artery would be blocked by the stent.

The Fischell patents also suggest that a wire with a radioisotope at its tip could be used to irradiate a dilated stenosis for preventing of restenosis. Although the concept of a temporarily placed radioisotope wire eliminates the need for the permanent implantation of a radioisotope stent, its fails to achieve two important objectives, namely, there is no means suggested for centering the wire in the artery, and a straight wire cannot correct an intimal dissection because it cannot exert a radially outward force over most of the inner surface of the dilated stenosis that would push the dissected plaque back against the arterial wall.

In U.S. Pat. No. 5,199,939 by M. D. Dake, et al, a wire with a radioisotope tip is again suggested that also has the two disadvantages stated above.

In U.S. patent application Ser. No. 08/408,780 filed on Mar. 23, 1995, (which is included herein by reference) the present inventors describe a temporary radioisotope stent that requires a somewhat complex deployment means but does have the advantage of placing a helical coil temporary stent with the capability of placing the isotope in direct contact with the wall of the dilated stenosis. Furthermore, the invention described in the application Ser. No. 08/408,780 is not capable of initially dilating a stenosis.

SUMMARY OF THE INVENTION

The purpose of the present invention is to overcome several of the shortcomings noted for all prior art devices designed to create and maintain the patency of a dilated arterial stenosis. Specifically, the invention described herein is a percutaneously inserted, temporary radioisotope stent system that utilizes an expandable balloon to push the stent radially outward against the wall of a dilated stenosis. This radially outward force on the interior wall of the dilated stenosis will cause any intimal dissection that may have occurred to be moved away from the central lumen of the artery and against the arterial wall, thereby immediately improving blood flow. If the dissected plaque is held against the vessel wall for an extended period of time (viz., one-quarter to 24 hours) that tissue will often be permanently retained on the arterial wall after the temporary stent is removed. Furthermore, after the balloon is deflated, a pusher tube can be used to maintain the stent in its expanded state against the arterial wall. This allows perfusion of distal tissue and furthermore allows blood flow into a side branch of the artery at the site of the dilated stenosis.

A stent is optimally shaped to provide a relatively uniform cylindrical radiation field to the arterial tissue of the dilated stenosis while minimizing the radiation source strength. This occurs because the stent's outer surface actually contacts the interior wall of the dilated stenosis along the entire length of the stent. This direct contact is particularly important for beta particle irradiation because beta particles have an extremely short range in blood or tissue. On the other hand, a single straight wire or catheters would typically touch only one side of the interior surface of the arterial wall which results in one portion of the dilated stenosis receiving too high a level of radiation while the opposite side is exposed to a markedly decreased radiation exposure level. Therefore, because of its very short range, beta particle irradiation is particularly disadvantageous when used with a wire or catheter even if it is centered in the artery. Furthermore, a simple wire is not able to exert an outward radial force along the length of the dilated stenosis so that it cannot efficiently push loosened plaque back against the arterial wall.

Therefore, a first objective of the invention is to use a conventional balloon angioplasty catheter to temporarily create a deployed stent within a dilated arterial stenosis to force loosened (i.e., dissected) plaque back against the inner surface of the arterial wall, which stent can be easily removed at some appropriate time after placement.

Another object of this invention is to maintain an outward force for an appropriate period of time so that the dissected plaque would permanently reattach itself to the arterial wall.

Still another object of this invention is to allow perfusion of distal tissue and blood flow to one or more arterial side branches within the dilated stenosis by deflating the balloon while utilizing a pusher tube to maintain the stent in its deployed state.

Still another object of this invention is to utilize a pusher tube to maintain the stent in its deployed state after the balloon is deflated.

Still another object of this invention is to place a radio-isotope within, or onto the surface of the temporary stent so as to decrease neointimal proliferation and thereby reduce the rate of restenosis.

Still another object of this invention is to optimize the irradiation of the tissue of dilated stenosis while requiring the lowest possible radioisotope source strength by having the outer surface of the stent pushed outwardly against the inner surface of the dilated stenosis.

Still another object of this invention is to have the temporary radioisotope stent with a comparatively low source strength as a disposable device as opposed to after-loading therapy wires (or catheters) that are highly radioactive and are very much more expensive and therefore must be reused.

Still another object of this invention is to be able to perform this entire procedure in a catherization laboratory by an interventional radiologist or cardiologist without exposing the interventionalist to any significant level of radiation from the temporary radioisotope stent.

Still another object of this invention is to be able to safely remove the temporary radioisotope stent system without the assistance of fluoroscopy.

Still another object of this invention is to irradiate the dilated stenosis for a period of time that is equal to or less than the time that it takes for heparin effects to wear off at the end of an angioplasty procedure so that irradiation therapy does not necessitate prolonged heparin therapy (which could delay arterial sheath removal).

Still another object of this invention is that a single system can be used for: (1) initial dilatation of the stenosis, (2) providing a prolonged radially outward force on the arterial wall to treat intimal dissection, (3) decreasing elastic recoil of the dilated stenosis, and (4) irradiating the dilated stenosis to decrease the rate of restenosis.

Still another object of this invention is to use a first means being either balloon angioplasty or atherectomy to initially open the arterial stenosis, and then using the present invention to perform items (2), (3) and (4) of the object described immediately above.

These and other objects and advantages of this invention will become apparent to a person of ordinary skill in this art upon careful reading of the detailed description of this invention including the drawings as presented herein.

DETAILED DESCRIPTION OF THE INVENTION

Figure 1:
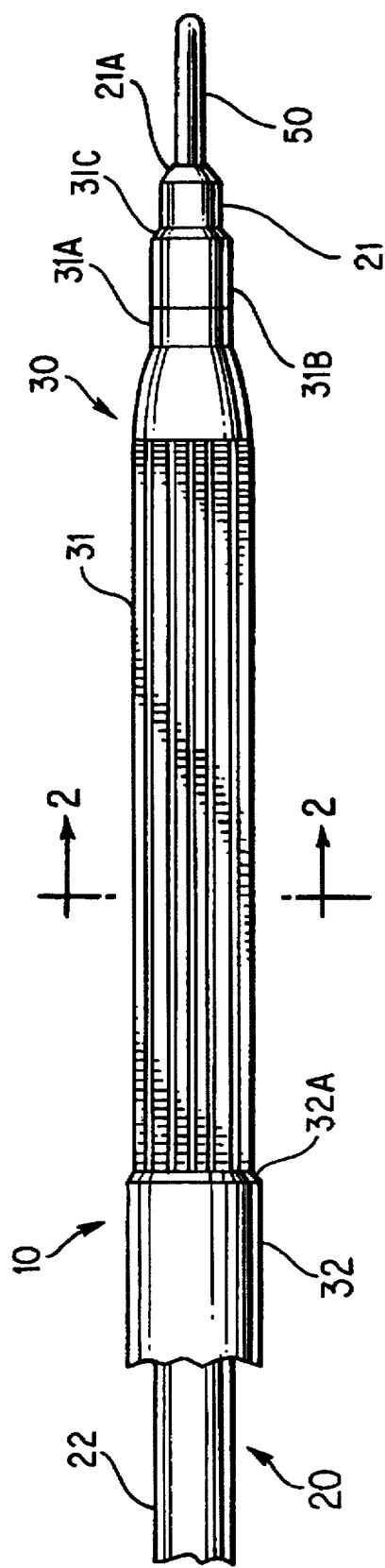
FIG. 1 is a side view of a distal section of the temporary radioisotope stent system.
Figure 2:
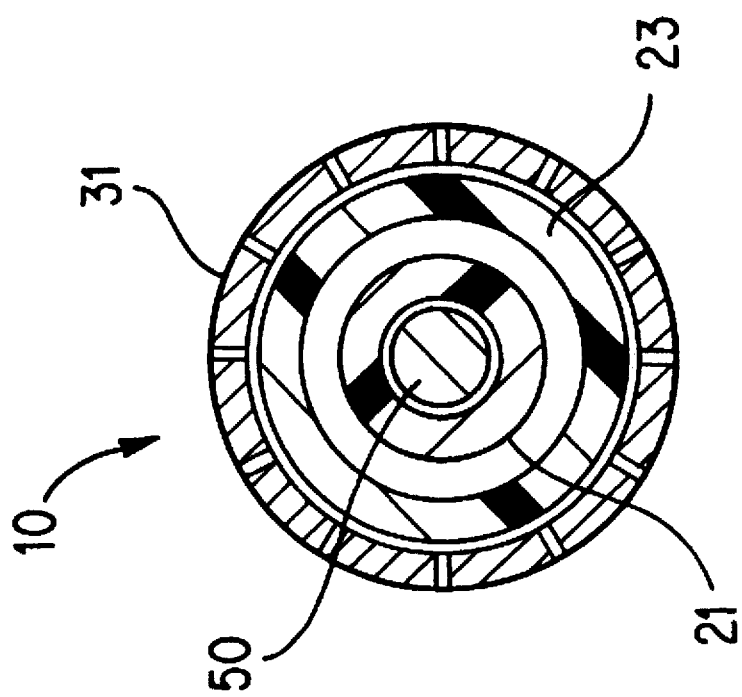
FIG. 2 is a transverse cross section of the balloon and stent at section 2—2 of FIG. 1 shown before balloon inflation.
Figure 3A:
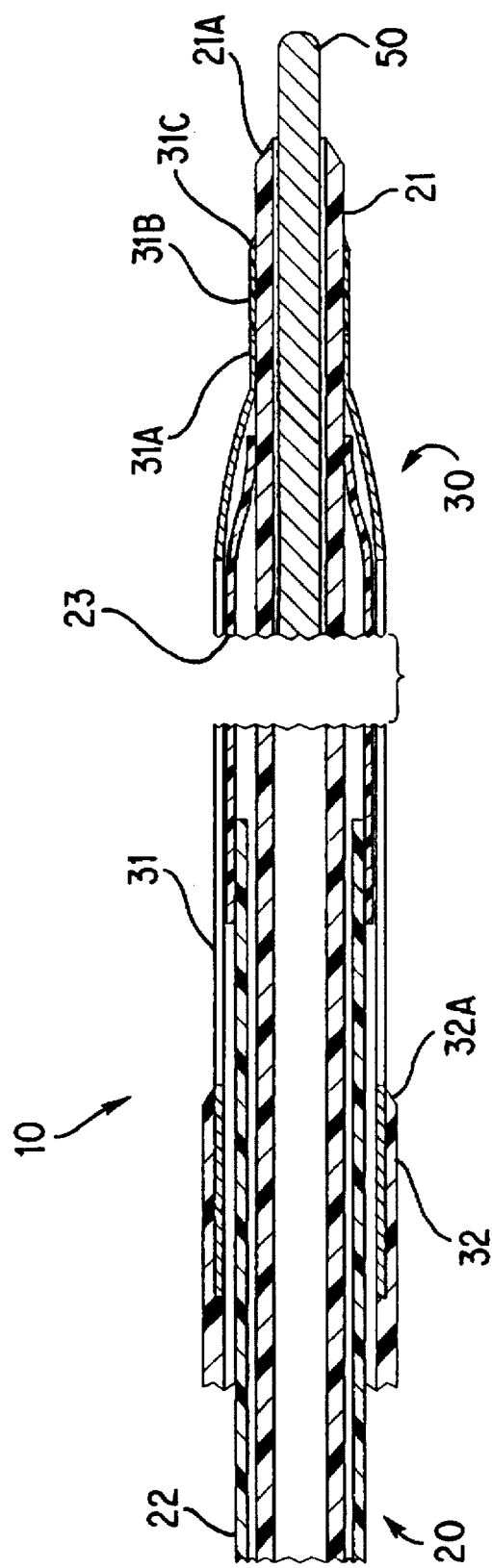
FIG. 3A is a longitudinal cross section of a distal section of the temporary radioisotope stent system.

FIG. 1 is a side view and FIG. 3A is a longitudinal cross section of a distal section of the balloon expandable temporary stent system 10 consisting of a conventional, over-the-wire balloon angioplasty catheter 20, a stent assembly 30, and a guide wire 50. FIG. 2 is a cross section of the system 10 at section 2—2 of FIG. 1. The pre-deployment state of the system 10 shown in FIGS. 1, 2 and 3A shows that the balloon angioplasty catheter 20 has an inner shaft 21 with a tapered distal end 21A, an outer shaft 22 and a balloon 23 shown in its pre-deployment state. The stent assembly 30 consists of a temporary, deployable stent 31 having a small diameter distal end portion 31A, a plastic tube 31B having a tapered adhesive portion 31C at its distal end, and a pusher tube 32 having a tapered distal end 32A. The distal end 31A of the stent 31 and the tube 31B are both adhesively bonded to the exterior surface of the inner shaft 21. A proximal section of the stent 31 is adhesively bonded to the pusher tube 32 as shown in FIG. 3A.

Figure 3B:
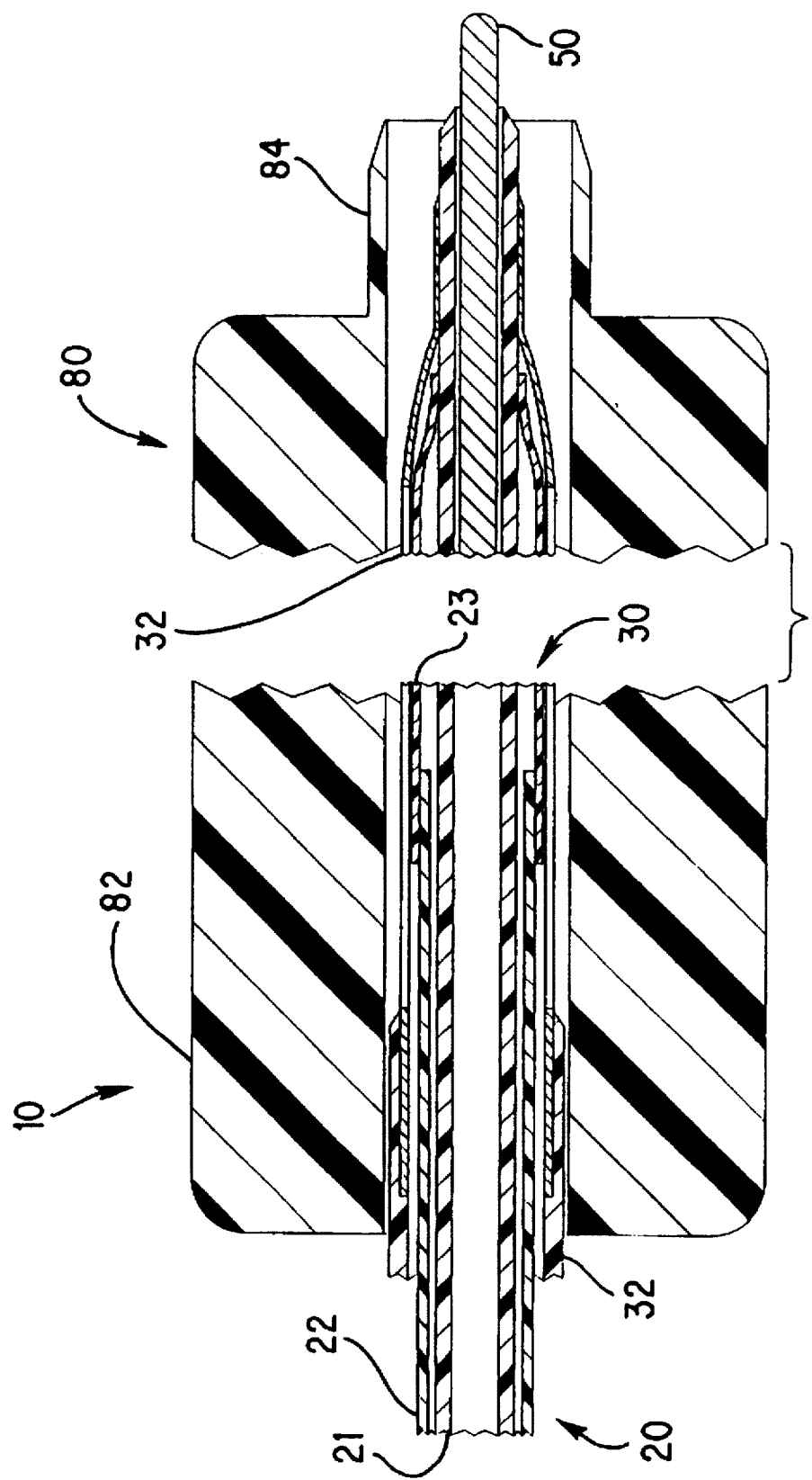
FIG. 3B is a longitudinal cross section of a distal section of the temporary radioisotope stent system including a radiation shield that surrounds the radioisotope stent.

FIG. 3B is longitudinal cross section of a distal section of the system 10 including a conventional balloon angioplasty catheter 20 having an inner shaft 21, outer shaft 22, balloon 23 and a temporary stent assembly 30 having a stent 31 and pusher tube 32. FIG. 3B also shows a guide wire 50 and a radiation shield 80 having a main body 82 and distal cylinder 84. The object of the shield 80 is to protect health care workers from exposure to radiation from the stent 31 if it is made to be radioactive. As described in the U.S. patent application Ser. No. 08/408,780, which is included herein by reference, the cylinder 84 can be inserted and locked into a Tuohy-Borst adaptor mounted onto a guiding catheter prior to insertion of the system 10 into the guiding catheter and thence into a human coronary (or other) artery.

Figure 4:
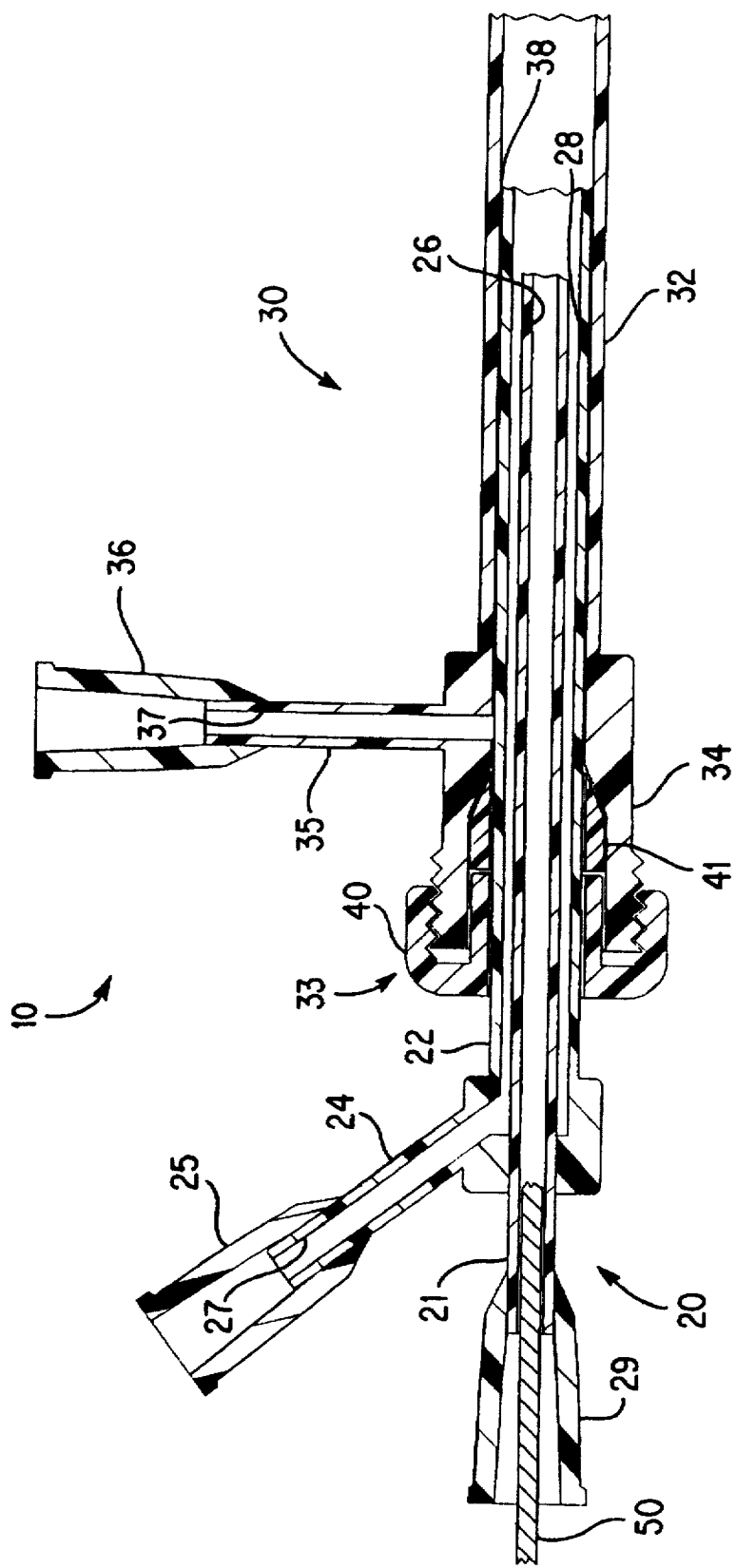
FIG. 4 is a longitudinal cross section of a proximal section of the temporary radioisotope stent system.

FIG. 4 is a longitudinal cross section of a proximal section of the system 10. The proximal section of the balloon angioplasty catheter 20 shows an outer shaft 22 and an inner shaft 21 having a lumen 26 through which the guide wire 50 can be slideably moved. The inner shaft 21 has a female Luer fitting 29 at its proximal end. The side arm 24 has female Luer fitting 25 and a lumen 27 which is in fluid communication with the annular passageway 28 that lies between the outer surface of the inner shaft 21 and the inner surface of the outer shaft 22. The Luer fitting 29 is used to flush the lumen 26 prior to placement of the guide wire 50. The Luer fitting 25 is attached to a source of pressurized fluid for inflating and deflating the balloon 23.

Also shown in FIG. 4 is the proximal section of the pusher tube 32 that is fixedly attached at its proximal end to a Tuohy-Borst fitting 33. The Tuohy-Borst fitting 33 has a main body 34 and a side arm 35 having a female Luer fitting 36. The side arm 35 has a lumen 37 that is in fluid communication with the annular passageway 38 that lies between the inner surface of the pusher tube 32 and the outer surface of the outer shaft 22 of the balloon angioplasty catheter 20. The Luer fitting 36 makes it possible to flush out the passageway 38 with (typically) a normal saline solution prior to placing the system 10 into an artery of a human body. The nut 40 is screwed onto a threaded section of the main body 34. Tightening down on the nut 40 causes the deformable elastomer gland 41 to be frictionally joined to the outer shaft 22. In this state, the pusher tube 32 will remain in a fixed position relative to the outer shaft 22. When the nut 40 is loosened, the pusher tube 32 can be pushed in a forward direction which, as described below, allows the balloon 23 to deploy the stent 31.

Figure 5:
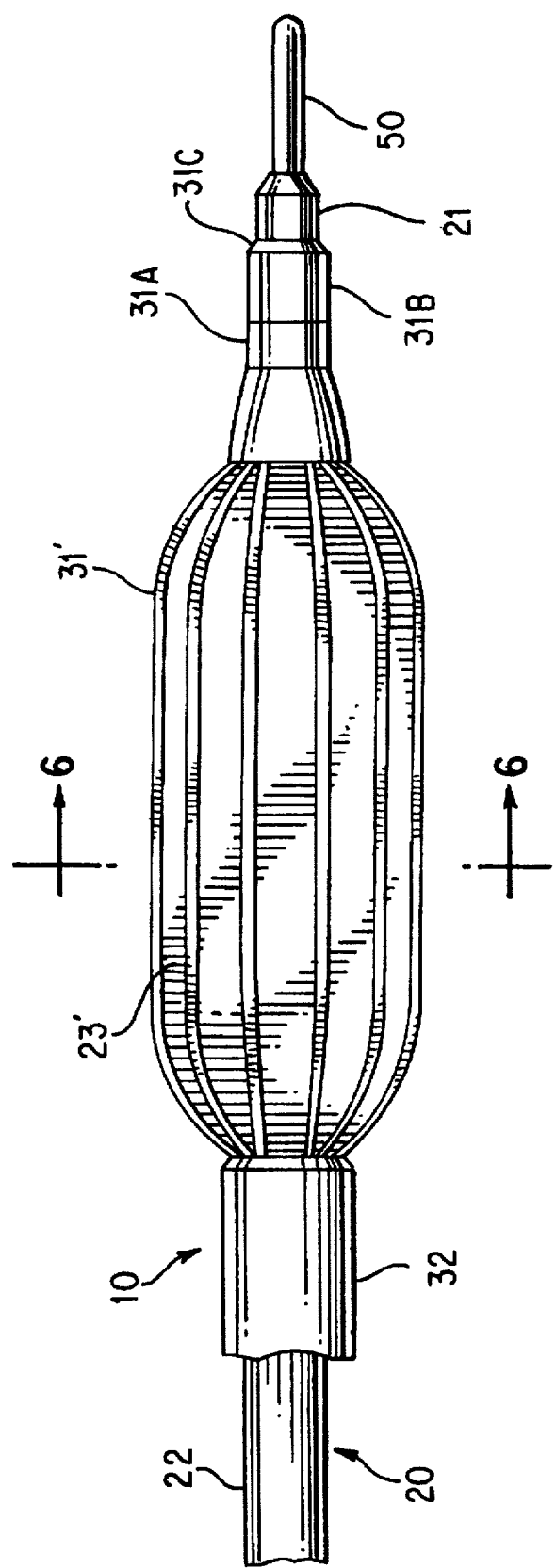
FIG. 5 is a side view of a distal section of the stent system with the balloon expanded and the stent deployed.

FIG. 5 shows the distal section of the system 10 in its deployed state with the expanded balloon 23' which would cause the metal spokes of the deployed stent 31' to be pushed against the wall of a dilated stenosis (not shown). Furthermore, the inflated balloon 23' can actually perform stenotic dilatation; i.e., balloon angioplasty. Furthermore, the balloon 23' can cause the spokes of the stent 31' to be pushed against the wall and into the plaque of a dilated stenosis.

Figure 6:
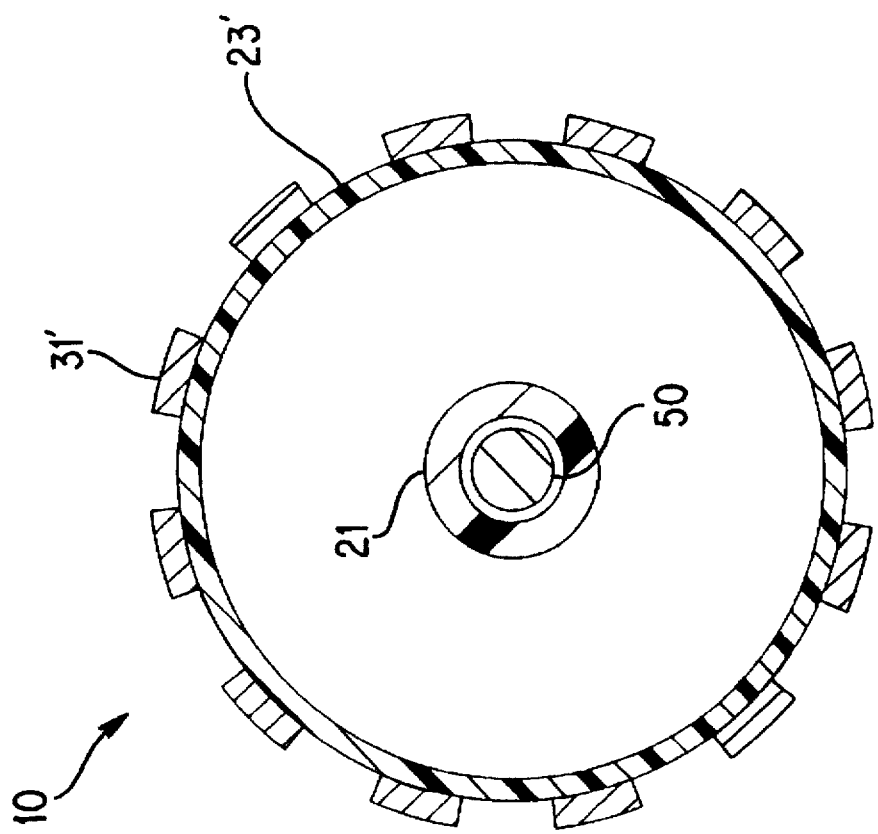
FIG. 6 is a transverse cross section of the balloon and stent at section 6—6 of FIG. 5 shown after balloon inflation.

FIG. 6 is a transverse cross section of the system 10 at section 6—6 of FIG. 5. FIG. 6 shows the inner shaft 21 surrounding the guide wire 50. The inflated balloon 23' can cause the deployed stent 31' to have its spokes be pushed radially outward with considerable force. This helps to drive the stent spokes firmly into the plaque for optimum irradiation of the dilated tissue.

Figure 7:
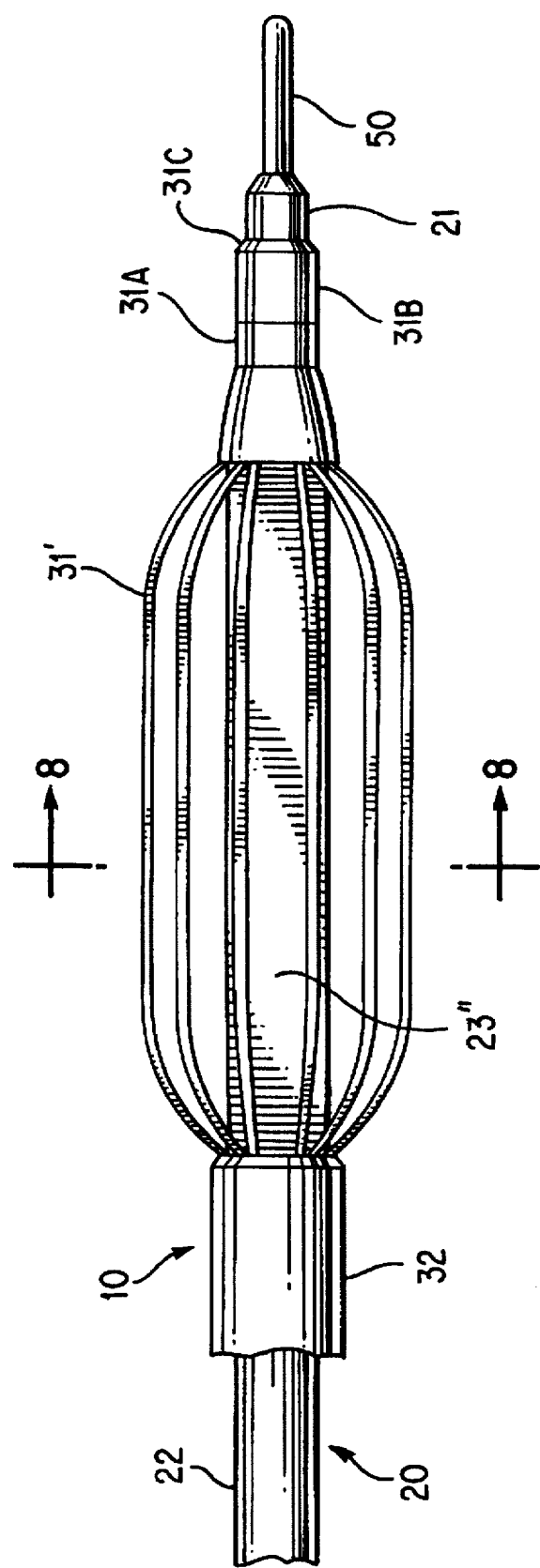
FIG. 7 is a side view of the distal section of the stent system showing the pusher tube pushed forward with the balloon deflated but with the stent maintained in its deployed state.
Figure 8:
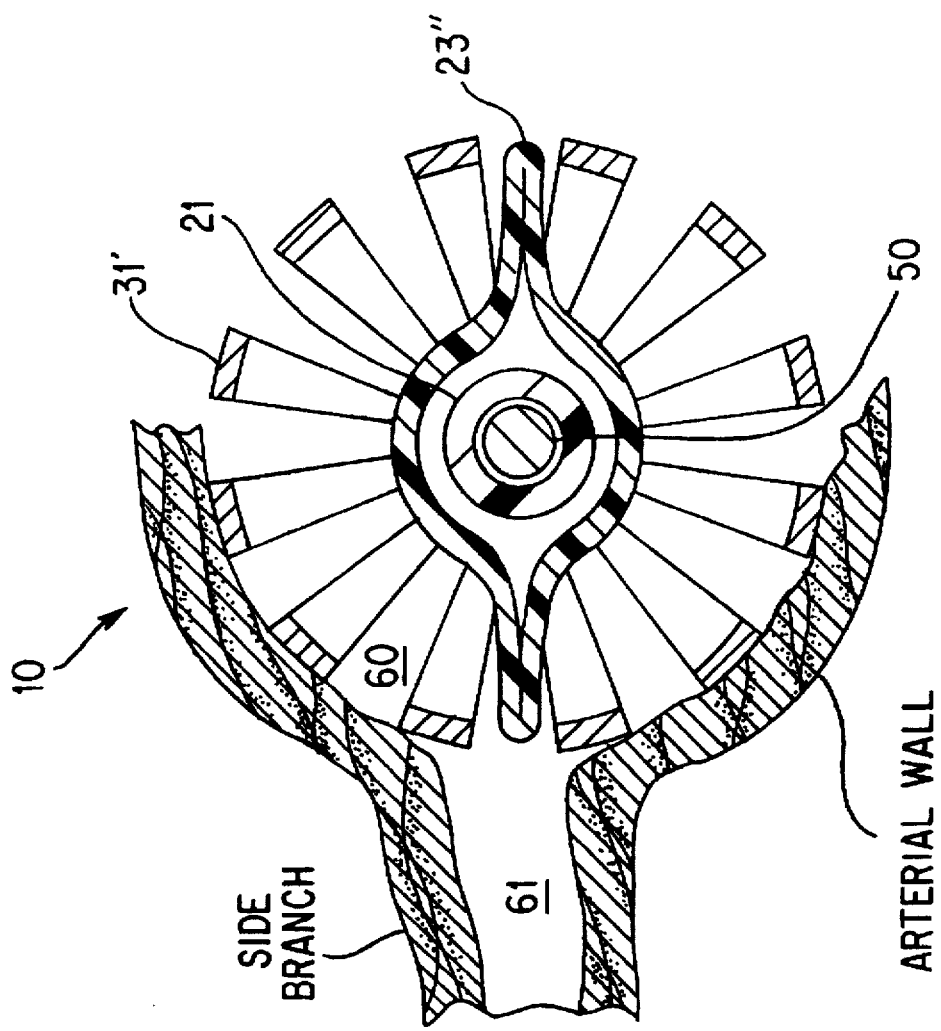
FIG. 8 is a transverse cross section of the temporary radioisotope stent system within a dilated stenosis of an artery with the balloon deflated and the stent in its deployed state.

Before the stent 31' is deployed radially outward as shown in FIGS. 5 and 6, the nut 40 of the Tuohy-Borst fitting 33 (see FIG. 4) is loosened so that the pusher tube 32 will be able to move in a forward (distal) direction when the balloon 23' is inflated. After the balloon 23' is inflated, the Luer fitting 29 is held fixed in one hand, while the operator's other hand is used to push the Tuohy-Borst fitting 33 forward (in a distal direction). The nut 40 is then tightened to frictionally attach the proximal end of the stent assembly 30 to the outer shaft 22 of the balloon angioplasty catheter 20. After this is accomplished, the inflated balloon 23' is deflated to form the balloon 23" having the shape as shown in FIGS. 7 and 8. Because the pusher tube 32 is pushing on the proximal end of the stent 31', and because the distal end of the stent 31' is fixedly attached to the inner shaft 21, the stent 31' will retain its deployed shape as shown in FIGS. 7 and 8 after the balloon is deflated.

FIG. 8 shows that the deflated balloon 23" typically forms "wings" around the inner shaft 21. However, the deflated balloon 23" allows the passageway 60 to be formed between the outside surface of the deflated balloon 23" and the inside surface of the arterial wall. In this state the arterial wall continues to experience an outwardly radial force from the deployed stent 31'. Since blood can readily flow through the passageway 60 and even into the lumen 61 of the side branch of the artery, perfusion and specifically oxygenation of the associated tissue is assured.

It should be understood that the deployed stent 31' obtains and holds its shape without exceeding the elastic limit of the metal from which the stent is typically made. Furthermore, after the deflated balloon 23" is formed and when the pusher tube 32 is pulled back relative to the inner shaft 21, the stent 31' will return to the shape of the predeployed stent 31 as shown in FIGS. 1, 2 and 3A. In that shape, it will wrap itself around the deflated balloon 23".

Figure 9:
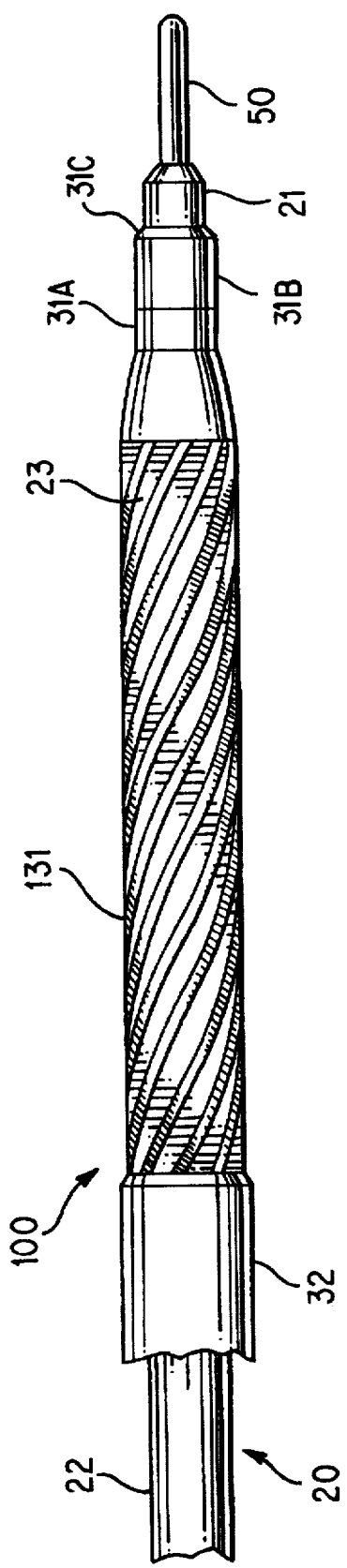
FIG. 9 is a side view of a distal section of an alternative embodiment of the temporary radioisotope stent wherein the stent is in the form of a helical coil.
Figure 10:
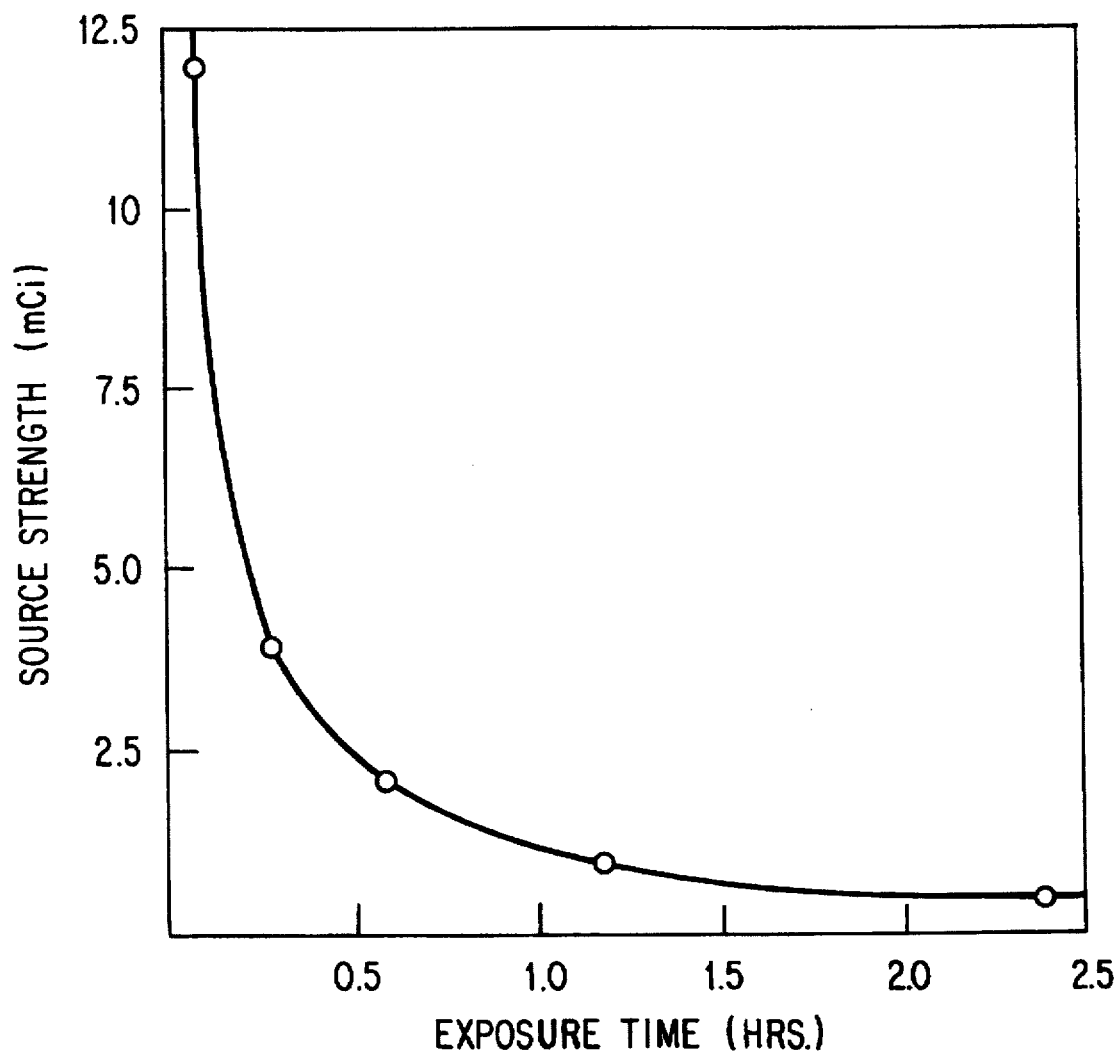
FIG. 10 illustrates the radioisotope source strength in milliCuries required to inhibit neointimal hyperplasia as a function of the exposure time of a dilated stenosis.

FIG. 9 shows a balloon expandable temporary stent system 100 that utilizes an alternative design stent 131. An important advantage of the design shown in FIG. 10 is that, when deployed, the helical coil type of stent 131 forms generally helical spokes that can exert considerably higher radial forces to prevent elastic recoil of the stenosis after dilatation as compared to the stent 31. The operation of the stent 131 would be the same as previously described for the stent 31, except that the pusher tube would be required to be advanced a somewhat greater distance in the distal direction as compared to the design of the system 10 in order to maintain the stent 131 pushing radially outward against the arterial wall.

Recent research has shown that exposing the dilated tissue to irradiation from a radioisotope source can dramatically reduce restenosis. Therefore, it is envisioned that the stent 31' could be plated with or have ion implanted or alloyed within its structure a radioisotope such as phosphorous 32. The effect of such an isotope is to prevent neointimal hyperplasia which is a principle cause of restenosis. The stent 31 (or 31') and/or balloon 23 (or 23' or 23") can also be coated with a heparin covalently bonded to a plastic substrate formed onto a metalic stent 31 or onto the outer surface of the balloon in order to decrease the formation of thrombus onto the stent or balloon surfaces.

FIG. 10 is a chart showing the number of milliCuries of phosphorous 32 that would be required to prevent arterial restenosis as a function of the time that the stent 31' is maintained in its deployed state. Even though as much as an hour might be necessary to obtain an adequate dose of radiation, since the passageway 60 provides for distal (and side branch) profusion, this comparatively long exposure time would not be a problem. Furthermore, an intimal dissection might be well treated by keeping the deployed stent 31' in place for times between 15 and 60 minutes. Thus, the present invention accomplishes the same result as a perfusion type balloon angioplasty catheter system with the added capability of providing irradiation of the dilated tissue.

After the pre-determined time period for irradiation has been achieved, the nut 40 (see FIG. 4) would be loosened, the Tuohy-Borst fitting 33 would be pulled back relative to the Luer fitting 29 of the balloon angioplasty catheter 20, and that would cause the stent to return to its pre-deployment shape, i.e., to the shape of stent 31 as shown in FIGS. 1, 2 and 3. The nut 40 could then be tightened down, and the entire system 10 could then be removed from the patient's arterial system.

The materials and dimensions of the balloon angioplasty catheter 20 and guide wire 50 are well known in the art of balloon angioplasty. The temporary stent 31 would typically be fabricated from a stainless steel such as type 316L or from a superelastic shape memory alloy such as Nitinol. The pusher tube 32 would typically be fabricated from a comparatively high durometer plastic such as polyurethane, polyethylene or PVC. The pusher tube 32 might also be formed from a thin-walled steel hypodermic tube for most of its length with a double wound, flat stainless steel wire distal section. The distal section would have good flexibility and pushability and would have a length of 5 to 30 cm with an outside diameter between 1 and 3 mm and a wall thickness between 0.1 and 0.5 mm.

Although the present invention describes a temporary radioisotope stent, it is also conceived that the conventional balloon angioplasty catheter 20 could have a radioisotope material ion implanted or otherwise formed into the balloon 23. Thus, when the balloon is expanded to provide dilatation of the stenosis, it could also irradiate the tissue to reduce restenosis. Perfusion could be accomplished by periodically deflating the balloon, for example for 15 seconds out of every minute.

Also balloon angioplasty could advantageously be accomplished with one of several perfusion balloon angioplasty catheters currently used by interventional cardiologists with a radioisotope implanted or otherwise formed into the balloon material.

It is also conceivable to utilize a special guide wire through which an oxygenated fluid can flow in order to perfuse distal tissue while using a conventional balloon angioplasty catheter with a radioisotope material situated within the balloon material. Alternatively, a radioactive liquid could be used to fill the balloon, thus providing a comparatively high source strength of radioactivity only where and when the balloon was filled with that radioactive liquid.

Although either the system 10 or 100 could be used by itself to perform both dilatation and irradiation of a stenosis, a preferred method of use could be to first perform balloon angioplasty or atherectomy with a separate device followed by the use of the system 10 or 100 to irradiate the dilated or atherectomized stenosis and/or to treat an intimal dissection while providing perfusion of distal tissue.

Still further, if a conventional perfusion balloon angioplasty catheter is used, one could utilize the temporary stent structure 31 or 131 without the need for the pusher tube 32. That is, the balloon 23 would be expanded, for as long as 15 to 60 minutes which would expose the dilated stenosis to adequate irradiation from a radioisotope formed within or plated onto the stent 31' while the inflated perfusion balloon allows blood to flow to the distal tissue.

Figure 11:
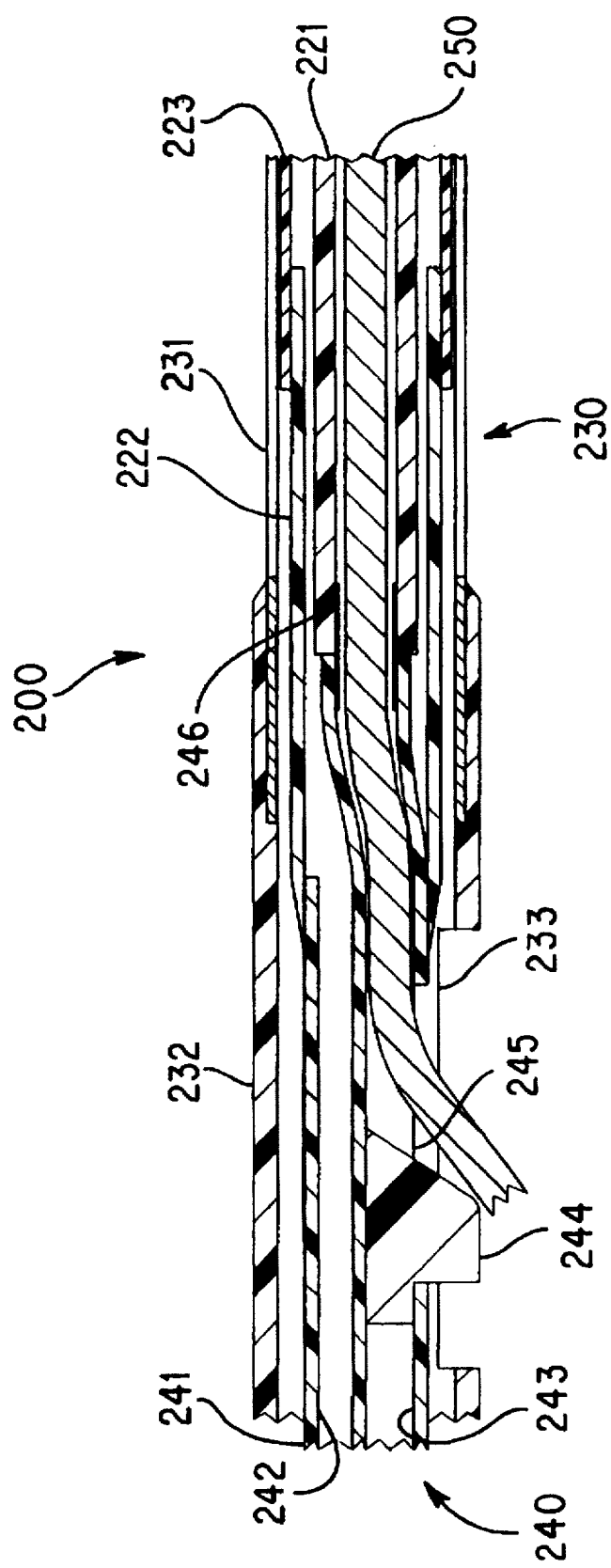
FIG. 11 is a longitudinal cross section of a "rapid exchange" alternative embodiment of the temporary balloon expandable stent system.

FIG. 11 is a longitudinal cross section of a "rapid exchange" type of balloon angioplasty stent system 200. The system 200 uses a conventional rapid exchange balloon angioplasty catheter with the type of stent assembly that has previously been described herein. Specifically, the rapid exchange balloon angioplasty catheter has a distal section which includes an inner shaft 221, an outer shaft 222 and an expandable balloon 223. This distal section is joined to a dual lumen main body 240, having an outer cylinder 241, a balloon inflation lumen 242 and a guide wire lumen 243 that is obstructed near its distal end by a guide wire deflector 244. The guide wire deflector 244 acts as a key in the slot 233 of the stent assembly 230 to prevent axial rotation of the assembly 230 relative to the outer cylinder 241. A thin-walled steel tube 246 joins the inner shaft 221 to the guide wire lumen 243 of the dual tureen main body 240.

The stent assembly 230 includes a temporary stent 231 and a pusher tube 232 into which a guide wire slot 233 is cut. The guide wire 250 enters through the slot 233 in the pusher tube 232, and then passes through the slot 245 into the distal continuation of the lumen 243, finally emerging from the distal end (not shown) of the inner shaft 221.

The system 200 operates in exactly the same manner as the previously described system 10, except that the guide wire 250 passes out of the system 200 close to its distal end rather than out its proximal end as shown in FIG. 4 for the conventional, over-the-wire, balloon angioplasty catheter. The advantage of the system 200 is that it can be used most conveniently after using a rapid exchange balloon angioplasty catheter to first perform stenotic dilatation followed by the use of the temporary stent system 200 in a manner as described herein.

Still further it is envisioned that a temporary stent system could be made without a balloon angioplasty catheter on the inner shaft 21. In this case, the pusher tube 32 would cooperate with the inner shaft 21 to provide deployment and retraction of the stent 31.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A system for creating a temporary stent within a vessel of a human body, the system comprising:

an over-the-wire balloon angioplasty catheter having a central lumen and a distal section having an inflatable balloon, the balloon angioplasty catheter having a proximal section that remains outside the body; and, a stent assembly slideably mounted onto the balloon angioplasty catheter in a coaxial relationship and having a proximal section and a distal section at which distal section is located a temporary stent whose distal end is fixedly attached to the distal section of the balloon angioplasty catheter, said balloon being fixedly secured to said distal section of said balloon angioplasty catheter, whereby said balloon and said temporary stent are fixedly positioned each to the other, the temporary stent's proximal end being fixedly attached to a distal end of an elongated pusher tube for cooperative positional relationship of said balloon and said temporary stent the pusher tube being adapted to cooperate with the proximal section of the balloon angioplasty catheter to cause the temporary stent to be reversibly deployed (1) radially outward responsive to inflation of said balloon and, (2) retracted so that the temporary stent reforms around the balloon of the balloon angioplasty catheter for providing blood flow through said vessel and removal of the system from the vessel of the human body.

2. The system of claim 1 further including a flexible guide wire that passes through the central lumen of the balloon angioplasty catheter.

3. The system of claim 1 wherein the temporary stent is formed from a multiplicity of metal spokes.

4. The system of claim 3 wherein the spokes prior to deployment are straight and extend in a longitudinal direction.

5. The system of claim 3 wherein each spoke is formed into a helical coil contour.

6. The system of claim 1 further comprising a radiation shield placed over the stent assembly.

7. The system of claim 1 wherein the stent assembly has a Tuohy-Borst fitting located at its proximal section.

8. The system of claim 1 wherein a least part of the temporary stent includes a radioisotope.

9. The system of claim 8 wherein the radioisotope emits beta particles.

10. The system of claim 8 wherein inflation of the balloon causes the spokes of the temporary stent to be deployed in a radially outward direction thereby causing dilatation and irradiation of a stenosis.

11. The system of claim 8 wherein the pusher tube remains in its most forward position to maintain an outward deployment of the radioisotope stent spokes while the balloon is deflated so that blood can pass through a space between a deployed temporary stent and the deflated balloon thereby perfusing tissue distal to the stent.

12. A system for creating a temporary stent within a vessel of a human body, the system comprising:

a flexible guide wire;

a rapid exchange balloon angioplasty catheter having distal and proximal sections, and being adapted for dilatation of an arterial stenosis, the balloon angioplasty catheter having an inner shaft and an outer shaft each having distal and proximal ends both shafts being located at the distal section of the balloon angioplasty catheter, and an inflatable balloon that connects the inner shaft to the outer shaft, the balloon angioplasty catheter having a lumen for the guide wire which exits from the distal end of the inner shaft with a lumen entry that is situated just proximal to the proximal end of the outer shaft, the balloon angioplasty catheter also having a proximal section that remains outside the body; and, a stent assembly coaxially mounted onto the balloon angioplasty catheter and having a proximal section and a distal section at which distal section is located a temporary stent whose distal end is fixedly attached near the distal end of the inner shaft of the balloon angioplasty catheter, the temporary stent's proximal end being fixedly attached to the distal end of an elongated pusher tube, the pusher tube having a guide wire entry slit situated near its distal end, and the pusher tube being adapted to cooperate with the proximal section of the balloon angioplasty catheter to cause the temporary stent to be deployed radially outward or to be retracted so that the temporary stent reforms around the balloon of the balloon angioplasty catheter for removal of the system from the vessel.

13. A balloon angioplasty catheter for dilating and irradiating a stenosis in a vessel of a human body, said balloon angioplasty catheter including a balloon having a source of radioactivity embedded into a material of said balloon.

14. The catheter of claim 13 wherein the balloon angioplasty catheter is an over-the-wire type.

15. The catheter of claim 13 wherein the balloon angioplasty catheter is a rapid exchange type.

16. The catheter of claim 13 wherein the balloon angioplasty catheter is adapted to provide perfusion of distal tissue.

17. The catheter of claim 13 wherein the source of the radioactivity is contained in an expandable layer which surrounds the balloon.

18. A method for treatment of an arterial stenosis comprising the following steps:

a) placing a temporary stent system formed from a stent assembly and a balloon angioplasty catheter into an artery of a human body, the stent assembly and the balloon angioplasty catheter each having a distal section and a proximal section, the balloon angioplasty catheter having an inflatable balloon located at its distal section and having a proximal section that is situated outside of the human body, the stent assembly having a temporary stent located at its distal section and an elongated pusher tube fixedly attached to the temporary stent and extending in a proximal direction, the pusher tube having a proximal section that extends outside the human body and includes a means for locking the proximal tube's proximal section to the proximal section of the balloon angioplasty catheter, b) expanding an inflatable balloon that is at the distal end of the balloon angioplasty catheter and within the temporary stent so as to push the stent radially outward against a stenosis, c) simultaneously applying a forward force at the proximal section of the stent assembly and a backward pull at the proximal section of the balloon angioplasty catheter, d) engaging the locking means on the stent assembly's proximal section to frictionally attach the stent assembly to the balloon angioplasty catheter, e) deflating the balloon, f) positionally maintaining said temporary stent in fixed position to expose an arterial wall in contact with the stent to be irradiated from a radioisotope source located on the stent, g) disengaging the locking means on the stent assembly's proximal section, h) simultaneously applying a backward force on the proximal section of the stent assembly while applying a forward force on the proximal section of the balloon angioplasty catheter, and i removing the temporary stent from the human body.

19. The method of claim 18 further comprising the following step of:

i allowing sufficient time to repair an intimal dissection.

20. The method of claim 19 further comprising the following step of:

k) providing a separate balloon angioplasty catheter to pre-dilate an arterial stenosis.

* * * * *